United States Patent [19]

Mori et al.

[11] Patent Number: 5,229,346
[45] Date of Patent: Jul. 20, 1993

[54] PROCESS FOR PRODUCING HYDROGENATION REACTION CATALYST PRECURSOR

[75] Inventors: Atsuhito Mori; Yasuyuki Hattori; Kiyoshi Tsukada; Noriaki Fukuoka, all of Wakayama, Japan

[73] Assignee: Kao Corporation, Tokyo, Japan

[21] Appl. No.: 886,398

[22] Filed: May 21, 1992

[30] Foreign Application Priority Data

May 22, 1991 [JP] Japan ................................. 3-117592
Oct. 28, 1991 [JP] Japan ................................. 3-281367

[51] Int. Cl.$^5$ .................... B01J 21/06; B01J 23/06; B01J 23/10; B01J 23/72
[52] U.S. Cl. .................................. 502/302; 502/303; 502/304; 502/306; 502/307; 502/309; 502/340; 502/342; 502/343; 502/346
[58] Field of Search ............... 502/303, 304, 309, 340, 502/342, 343, 346, 302, 306, 307

[56] References Cited

U.S. PATENT DOCUMENTS 5,011,806  4/1991  Irick et al. ..................... 502/343

FOREIGN PATENT DOCUMENTS 63-141937  6/1988  Japan ..................... 502/343

Primary Examiner—W. J. Shine
Attorney, Agent, or Firm—Sughrue, Mion, Zinn, Macpeak & Seas

[57] ABSTRACT

A process for producing a hydrogenation reaction catalyst precursor is disclosed, including the steps of:

(i) coating the outer surface of at least one of a first titanium oxide and a first titanium hydroxide having an outer surface area of at least 15 m$^2$/g with at least one of a second titanium oxide and a second titanium hydroxide formed by hydrolyzing at least one of a titanium alkoxide represented by Formula (I) and a titanium alkoxo acid represented by Formula (II) to prepare a catalyst carrier (A);

$$Ti(OR)_4 \qquad (I)$$

wherein R represents an alkyl group having from 1 to 18 carbon atoms or an aryl group, $$H_2[Ti(OR)_6] \qquad (II)$$

wherein R has the same meaning as above;

(ii) applying a metal oxide composition (B) onto the catalyst carrier (A) obtained in step (i), or mixing the metal oxide composition (B) with the catalyst carrier (A) to obtain a hydrogenation reaction catalyst precursor. Also, a process for producing an alcohol is described, including catalytically reducing an organic carboxylic acid ester with hydrogen in the presence of a catalyst obtained by reducing the hydrogenation reaction catalyst precursor produced by the process described above.

7 Claims, No Drawings

PROCESS FOR PRODUCING HYDROGENATION REACTION CATALYST PRECURSOR

FIELD OF THE INVENTION

The present invention relates to a process for producing a hydrogenation reaction catalyst precursor, and to a process for producing an alcohol using the catalyst precursor.

BACKGROUND OF THE INVENTION

A process for producing an alcohol has been proposed using a copper-zinc catalyst precursor carried on titanium oxide in JP-A-1-305042 (the term "JP-A" as used herein means an "unexamined published Japanese patent application"), but it has been found that when a titanium oxide which is usually available is used as the carrier, there is generally the following problem in regard to the catalytic performance.

That is, when the titanium oxide which is used has a low surface area, a sufficient reaction activity is not obtained, and when a high-purity titanium oxide prepared from titanium sulfate or titanium chloride is used, a reduction of the reaction selectivity caused by the presence of a slight amount of an impurity (a sulfate ion or a chloride ion) is observed.

Furthermore, when the foregoing catalyst using a titanium oxide which is usually available as a carrier is subjected, for example, to tablet-forming working, the catalyst is inferior in moldability and strength.

The foregoing problem is overcome by using titanium oxide and/or titanium hydroxide obtained by the hydrolysis of an alkoxide of titanium as the carrier in place of a titanium oxide carrier which is usually available. However, the catalyst precursor using this titanium oxide and/or titanium hydroxide as a carrier has the problem of high cost, since the carrier is very expensive.

On the other hand, a process for producing a titanium oxide carrier by coating active titanium oxide on a base material composed of titanium oxide porcelain is described in JP-A-52-48582. According to the process, to provide a sufficient mechanical strength for the molded carrier, it is necessary to use a titanium oxide base material obtained by burning at a high temperature of from 900° C. to 1300° C., and also it is desirable that the coating amount of active titanium oxide is at least 100% by weight, based on the weight of the titanium oxide base material. However, since the surface area of the titanium oxide base material becomes very low due to burning at a very high temperature, even when such a titanium oxide base material is coated with active titanium oxide, the product obtained does not show a sufficient reactivity.

SUMMARY OF THE INVENTION

As the result of various investigations of the foregoing problems, the inventors have discovered that the foregoing problems can be solved by a process for producing a hydrogenation reaction catalyst precursor comprising the steps of:

(i) coating the outer surface of at least one of a first titanium oxide and a first titanium hydroxide having an outer surface area of at least 15 m²/g with at least one of a second titanium oxide and a second titanium hydroxide formed by hydrolyzing at least one of a titanium alkoxide represented by Formula (I) and a titanium alkoxo acid represented by Formula (II) to prepare a catalyst carrier (A);

Ti(OR)₄  (I)

wherein R represents an alkyl group having from 1 to 18 carbon atoms or an aryl group,

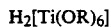

H₂[Ti(OR)₆]  (II)

wherein R has the same meaning as above;

(ii) applying a metal oxide composition (B) comprising copper oxide and optionally at least one of zinc oxide and at least one oxide of a metal selected from an element of group IIa of the periodic table, an element of group IIIb of the periodic table, a lanthanide element, and an actinide element in a weight ratio of 100:(0 to 25):(0 to 25), onto the catalyst carrier (A) obtained in step (i), or mixing the metal oxide composition (B) with the catalyst carrier (A) at a weight ratio of (B)/(A)=15/85 to 65/35 to obtain a hydrogenation reaction catalyst precursor, and by a process for producing an alcohol comprising catalytically reducing an organic carboxylic acid ester with hydrogen in the presence of a catalyst obtained by reducing the hydrogenation reaction catalyst precursor produced according to the process described above.

DETAILED DESCRIPTION OF THE INVENTION

Each step of the present invention is described in detail below.

Step (i)

Titanium oxide and/or titanium hydroxide having an outer surface area of at least 15 m²/g to be used in this invention (hereinafter referred to as the titanium oxide/hydroxide base material) is prepared by drying and/or burning titanium sulfate or titanium chloride at a temperature of usually from 50° C. to 800° C., preferably 150° to 600° C. The titanium oxide/hydroxide base material thus obtained usually contains a slight amount of impurities originated in the raw material, and thus if the base material is used as a hydrogenation catalyst carrier, the selectivity of the hydrogenation reaction is lowered.

According to the present invention, the foregoing titanium oxide/hydroxide base material is not used as a hydrogenation catalyst carrier, but rather it is coated with titanium oxide and/or titanium hydroxide formed by hydrolyzing the titanium alkoxide represented by Formula (I) and/or the titanium alkoxo acid represented by Formula (II) (hereinafter referred to as the coating titanium oxide/hydroxide), whereby the lowering of the selectivity of the hydrogenation reaction can be prevented.

Examples of the titanium compounds represented by Formula (I) and/or Formula (II) include titanium tetramethoxide Ti(OCH₃)₄, titanium tetraethoxide Ti(OC₂H₅)₄, titanium tetraisopropoxide Ti(OC₃H₇)₄, titanium tetra-n-butoxide Ti(OC₄H₉)₄, titanium tetrakis-2-ethylhexoxide Ti[OCH₂CH(C₂H₅)C₄H₉]₄, titanium tetrastearoxide Ti(OC₁₈H₃₇)₄, titanium hexaisopropoxo acid H₂[Ti(OC₃H₇)₆], titanium hexamethoxo acid H₂[Ti(OCH₃)₆], titanium hexaethoxo acid H₂[Ti(OC₂H₅)₆], titanium hexa-n-butoxo acid H₂[Ti(OC₄H₉)₆], etc.

The amount of the at least one of a second titanium oxide and a second titanium hydroxide (hereinafter referred to as coating titanium oxide/hydroxide) is from 5 to 100% by weight, and preferably from 10 to 50% by weight, based on the weight of the at least one of a first titanium oxide and a first titanium hydroxide (hereinafter referred to as titanium oxide/hydroxide base material). If the amount of coating titanium oxide/hydroxide is lower than the aforesaid range, the selectivity of the hydrogenation reaction is lowered. On the other hand, if the amount of coating titanium oxide/hydroxide is higher than the aforesaid range, the obtained catalyst carrier is undesirable from an economical point of view.

The outer surface area of the at least one of a first titanium oxide and a first titanium hydroxide (i.e., the titanium oxide/hydroxide base material) to be used in this invention is an important factor for determining the catalytic activity and is desired to be larger in general, which is at least 15 m²/g, preferably at least 50 m²/g, as measured by the BET method, from the viewpoint of the hydrogenation reactivity. If the outer surface area is less than 15 m²/g, the necessary hydrogenation reactivity is not obtained.

In the present invention, there is no particular restriction on the process for coating the coating titanium oxide/hydroxide on the titanium oxide/hydroxide base material, and suitable processes include a process of hydrolyzing the titanium compounds of Formula (I) and/or Formula (II) in the presence of the titanium oxide/hydroxide base material to precipitate the coating titanium oxide/hydroxide thus formed on the outer surface of the base material, a process of blowing the titanium compounds of Formula (I) and/or (II) onto the titanium oxide/hydroxide base material and then bringing steam into contact the base material to hydrolyze the titanium compounds, etc.

Step (ii)

Either without or after burning at 150° to 600° C. the catalyst carrier (A) obtained in step (i), the metal oxide composition (B) as a catalytic active component is applied onto or mixed with the catalyst carrier (A) to obtain a hydrogenation reaction catalyst precursor.

The weight ratio of the metal oxide composition (B) to the catalyst carrier (A) may be 15:85 to 65:35, preferably 20:80 to 60:40, for obtaining high reactivity and selectivity of the catalyst.

The metal oxide composition (B) comprises (a) copper oxide and optionally at least one of (b) zinc oxide and (c) at least one oxide of a metal selected from an element of group IIa of the periodic table, an element of group IIIb of the periodic table, a lanthanide element and an actinide element in the weight ratio of 100:(0 to 25):(0 to 25), preferably 100:(1 to 20):(1 to 20).

If the ratio of (b) and (c) to (a) is over the upper limit of the largest disclosed range, the selectivity is sufficient, but the catalyst becomes disadvantageous in regard to its activity.

The elements belonging to group IIa for use in this invention are Be, Mg, Ca, Sr, Ba, and Ra; the elements belonging to group IIIb which are suitable for this invention include Sc and Y; the lanthanide elements which can be used in this invention are La, Ce, Pr, Nd, Pm, Sm, Eu, Gd, Tb, Dy, Ho, Er, Tm, Yb, and Lu, and the actinide elements which can be used in this invention are Ac, Th, Pa, U, Np, Pu, Am, Cm, Bk, Cf, Es, Fm, Md, No, and Lr. They are used for the preparation of the catalyst singly or as a mixture thereof. Preferable examples of the metal oxide composition (B) include $CuO$-$ZnO$-$BaO$, $CuO$-$ZnO$-$MgO$, $CuO$-$ZnO$-$CaO$, $CuO$-$ZnO$-$Y_2O_3$, $CuO$-$ZnO$-$La_2O_3$, $CuO$-$BaO$, $CuO$-$MgO$, $CuO$-$CaO$, $CuO$-$Y_2O_3$ and $CuO$-$La_2O_3$.

In this invention, for improving the life of the catalyst, tungsten oxide ($WO_3$) and/or molybdenum oxide ($MoO_3$) may be added to the metal oxide composition as the catalytic activity component, as described in JP-A-3-220143.

There is no limitation in regard to the method for applying the metal oxide composition (B) on the catalyst carrier (A) or mixing them, but it is preferable to employ the method described in JP-A-1-305042 as follows.

That is, a precipitating agent can be added to a solution of a salt (e.g., a sulfate, nitrate, ammonium complex salt, acetate, oxalate, acetyl acetonate, or chloride) of the foregoing metals in the presence of the catalyst carrier (A), preferably at a pH of from 2 to 11, followed by burning the precipitate obtained. Examples of precipitating agents to be used in the above process include alkaline solutions such as ammonia, urea, ammonium carbonate, sodium carbonate, sodium hydroxide and potassium hydroxide.

Alternatively, the same metal salts can be impregnated in and carried on the catalyst carrier (A) in the solution thereof followed by burning.

Furthermore, compounds such as the oxide, hydroxide and carbonate of both the catalyst carrier (A) and the metals can be mixed uniformly followed by burning.

In the above processes, the burning step may be carried out at a temperature of from 300° to 600° C. in an oxidizing atmosphere.

The catalyst precursor thus obtained may further contain a slight amount of graphite, fatty acid salts, starch, mineral oil, talc, bentonite, alkali metal salts, etc., for increasing the catalyst strength.

The catalyst precursor thus obtained may be used in the form of a powder, but it can also be used in the form of pellets by molding the powder into pellets, which represents the superiority of the present invention in regard to the molding property and the strength of the molding.

Hydrogenation Reaction

The catalyst precursor obtained as described above is reduced to a catalyst for a hydrogenation reaction and used for producing, for example, an alcohol by hydrogenating an organic carboxylic acid ester.

In reduction-activating the catalyst precursor, a vapor-phase reduction method or a liquid-phase reduction method carrying out the reduction in a hydrocarbon such as liquid paraffin, etc., or in a solvent such as dioxane, an aliphatic alcohol, a fatty acid ester, etc., may be used. For example, in the case of reducing the catalyst precursor by using hydrogen gas, it is preferred to carry out the reduction at a temperature of from 100° to 800° C., preferably from 150° to 500° C., until the formation of water is not observed or until the absorption of hydrogen is not observed. In particular, in the case of carrying out the reduction in a solvent, it is preferred to carry out the reduction at a temperature of from 150° to 350° C., until the absorption of hydrogen is not observed. Furthermore, an ordinary activation method of reducing the catalyst precursor in an organic carboxylic acid ester which is a raw material for the hydrogenation at a raised temperature in a hydrogen reducing atmosphere and using the reduced catalyst precursor for the reaction can be used without causing any problem.

Suitable reducing agents which can be used in reducing the catalyst precursor include hydrogen, carbon monoxide, ammonia, hydrazine, formaldehyde, and a lower alcohol such as methanol, etc., and they may be used singly or as a mixture thereof. Also, the reducing agent may be used in a diluted state with an inert gas such as nitrogen, helium, argon, etc., or in the presence of a small amount of steam.

Examples of the organic carboxylic acid ester to be used as a starting material of an alcohol in the invention include esters of alicyclic carboxylic acids, aromatic carboxylic acids, and aliphatic carboxylic acids such as esters of a straight or branched chain saturated or unsaturated fatty acid. By hydrogenating these esters, the carboxylic acid moieties are reduced to form the corresponding alcohols. There is no particular restriction on the alcohol moiety constituting the carboxylic acid ester but typical examples thereof include straight-chain or branched and saturated or unsaturated alcohols having 1 to 24 carbon atoms. Specific examples thereof include methanol, ethanol, 1-propanol, 2-propanol, 1-butanol, 2-butanol, 2-ethylhexanol, 2,2-dimethyl-1,3-propanediol, ethylene glycol, propylene glycol, 1,4-butanediol, 1,6-hexanediol, 1,10-decanediol, cyclohexanol, benzyl alcohol, diethylene glycol, glycerol and trimethylolpropane. Specific examples of organic carboxylic acid esters suitable for the present invention include formic acid esters, acetic acid esters, caproic acid esters, caprylic acid esters, undecenic acid esters, lauric acid esters, myristic acid esters, palmitic acid esters, stearic acid esters, isostearic acid esters, oleic acid esters, oxalic aid esters, maleic acid esters, adipic acid esters, sebacic acid esters, cyclohexanecarboxylic acid esters, benzoic acid esters, and phthalic acid esters.

In hydrogenating the foregoing carboxylic acid ester, a suspensoid bed reaction system, a fixed bed reaction system, or a fluid bed reaction system may be employed depending on the form of the catalyst.

For example, in the case of employing a suspensoid bed reaction system, the powder form catalyst may be used. The reaction can be carried out using a solvent which does not adversely affect the reaction, such as alcohol, dioxane, or a hydrocarbon, but it is preferred to carry out the reaction without using a solvent for purposes of productivity. The amount of the catalyst is preferably from 0.1 to 20% by weight, based on the carboxylic acid ester, but it can be optionally selected in the range wherein a practical reaction rate is obtained, depending on the reaction temperature and the reaction pressure. The reaction temperature is from 160° C. to 350° C., preferably from 180° C. to 280° C., and the reaction pressure is from 1 to 350 kg/cm$^2$, preferably from 30 to 300 kg/cm$^2$.

Also, in the case of employing a fixed bed reaction system, the catalyst form which is suitable for the system is used. The reaction temperature is from 130° C. to 300° C., preferably from 160° C. to 270° C., and the reaction pressure is from 0.1 to 300 kg/cm$^2$. The liquid hourly space velocity (LHSV) is optionally determined depending on the reaction condition, but it is preferably in the range of from 0.5 to 5 for purposes of productivity and reactivity.

The catalyst precursor for a hydrogenation reaction produced by the process of the present invention provides a catalyst with very good activity and selectivity. In the case of molding the catalyst precursor into tablets, the catalyst precursor has an excellent molding property, and the tablets obtained show excellent mechanical strength.

Using the catalyst precursor obtained according to the present invention, a high quality alcohol can be produced at a high yield and with high selectivity by catalytically reducing the corresponding organic carboxylic acid ester with hydrogen at a practical reaction rate, even at a low temperature and a low pressure.

The invention will now be described in more detail by the following examples, but it should be noted that the invention is not limited to these examples. Unless otherwise indicated, all parts, percents, ratios, and the like are by weight.

EXAMPLE 1

Preparation of Catalyst Precursor

Titanium oxide (prepared by hydrolyzing titanium sulfate, using a burning temperature of 350° C., with the surface area of the titanium oxide being 150 m$^2$/g), which became a carrier base material, was suspended in isopropyl alcohol and after adding tetraisopropyl titanate $\{[(CH_3)_2CHO]_4Ti\}$ such that the concentration thereof became 10% by weight, based on the base material calculated as titanium oxide, followed by sufficiently stirring, water in the amount necessary for the hydrolysis was added thereto to form a coating of titanium hydroxide on the outer surface of the base material. After completely finishing the hydrolysis, the isopropyl alcohol in the system was distilled off. Thereafter, by mixing the residue with an aqueous solution of a mixture of copper nitrate and zinc nitrate and an aqueous solution of 10% by weight sodium carbonate with stirring at 98° C., a catalyst precursor slurry was obtained. Precipitates were separated from the slurry by filtration, sufficiently washed with water, and then dried to provide a catalyst precursor. The catalyst precursor obtained had the following weight composition:

$$CuO:ZnO:TiO_2 = 38\%:2\%:60\%$$

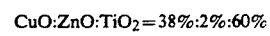

The powder of the catalyst precursor thus obtained was formed into tablets having a diameter of 3 mm, and after burning the tablets in an oxidizing atmosphere for 2 hours at a temperature of 450° C., the activity of the catalyst was evaluated.

Catalyst Activity and Selectivity Evaluation 15 g of the catalyst precursor thus formed into tablets was placed in an autoclave-type basket reactor together with 200 g of lauryl alcohol, and then the reductive activation of the catalyst precursor was carried out at a hydrogen pressure of 10 kg/cm$^2$ (gauge pressure) and a temperature of 200° C. for 2 hours under a hydrogen stream.

After finishing the reduction, lauryl alcohol was replaced with 200 g of a palm kernel $C_6$ to $C_{20}$ fatty acid methyl ester [saponification value (SV)=250 mg KOH/g, iodine value (IV)=177 Ig/100g], the reaction was carried out under a hydrogen gas stream at a hydrogen pressure of 120 kg/cm$^2$ (gauge pressure), a temperature of 230° C., and a stirring rate of 900 r.p.m. The primary reaction rate constant k was calculated from SV with the passage of time according to the formula $\ln[(SVo-SVe)/(SVt-Sve)]=kt$ (wherein SVo is the initial SV, SVe is the SV at balance and SVt is the SV after passage of time t), as an indicator of the catalyst activity.

Also, the sample was analyzed with capillary gas chromatography with the passage of time, and the content (%) of methyl ether and hydrocarbon when the saponification value (SV) was 10 mg KOH/g was obtained using the analysis value and was used as an indication of the catalyst selectivity.

The results obtained are shown in Table 1.

EXAMPLE 2

Titanium oxide as used in Example 1 as the carrier base material was suspended in isopropyl alcohol, tetra-isopropyl titanate {[(CH$_3$)$_2$CHO]$_4$Ti} was added to the suspension at 5% by weight to the base material calculated as titanium oxide, and a coating of titanium hydroxide was formed on the surface of the base material by hydrolysis. Then, by following the same method as in Example 1, a catalyst precursor formed into tablets was obtained, and the activity and selectivity thereof was evaluated in the same manner as in Example 1. The results obtained are shown in Table 1.

EXAMPLE 3

By following the same procedure as in Example 1 except that titanium oxide (burning temperature: 700° C; surface area: 20 m$^2$/g), which became the carrier base material, was added to isopropyl alcohol and suspended therein, a catalyst precursor was obtained, and the activity and selectivity of the catalyst was evaluated. The result obtained is shown in Table 1.

EXAMPLE 4

Titanium oxide as used in Example 1 as the carrier base material was suspended in isopropyl alcohol, tetra-isopropyl titanate {[(CH$_3$)$_2$CHO]$_4$Ti} was added to suspension at 2% by weight to the base material calculated as titanium oxide, and a coating of titanium hydroxide was formed on the surface of the base material by hydrolysis. Then, by following the same method as in Example 1, a catalyst precursor formed into tablets was obtained, and the activity and selectivity thereof were evaluated in the same manner as in Example 1. The results obtained are shown in Table 1.

COMPARISON EXAMPLE 1

Using titanium oxide (burning temperature: 350° C.; surface area: 150 m$^2$/g) as in Example 1 as the base material of the carrier, an aqueous solution of a mixture of copper nitrate and zinc nitrate, and an aqueous solution of 10% by weight sodium carbonate, with stirring the mixture at 98° C., a slurry having a pH of 9 was obtained. Precipitates were recovered from the slurry by filtration, washed sufficiently with water, dried, and then burned at 450° C. for 2 hours to provide a composite oxide of copper oxide-zinc oxide carried on titanium oxide. The composite oxide obtained had the following weight composition:

CuO:ZnO:TiO$_2$ = 38%:2%:60%

Then, by following the same method as in Example 1, a molded catalyst precursor was obtained, and the activity and selectivity thereof was evaluated as in Example 1. The result obtained is shown in Table 1.

COMPARISON EXAMPLE 2

Titanium oxide as used as the base material for the carrier in Example 1 was burned at a temperature of 900° C. for one hour in an oxidizing atmosphere to provide a titanium oxide powder having an outer surface area of 13 m$^2$/g. The foregoing titanium oxide powder was suspended in isopropyl alcohol, tetraisopropyl titanate was added to the suspension at 10% by weight based on the base material calculated as titanium oxide, and a coating of titanium hydroxide was formed on the surface of the base material by hydrolysis. Then, by following the same method as in Example 1, a composite oxide of copper oxide-zinc oxide carried on titanium oxide was obtained. The composite oxide obtained had the following weight composition:

CuO:ZnO:TiO$_2$ = 38%:2%:60%

Then, by following the same method as in Example 1, a molded catalyst precursor was obtained, and the activity and selectivity thereof was evaluated in the same manner as in Example 1. The result obtained is shown in Table 1.

TABLE 1

| | Base Material[1] | | Coated Amount | | Selectivity[3] | | | |
| | CuO:ZnO:TiO$_2$ (weight ratio) (%) | Outer Surface Area (m$^2$/g) | to Base Material (wt %) | Rate Constant K[2] (Hr$^{-1}$) | Hydro-carbon (%) | Methyl Ether (%) | Mold-ability[4] | Molding Strength[5] (kg/pellet) |
| --- | --- | --- | --- | --- | --- | --- | --- | --- |
| Example 1 | 38:2:60 | 150 | 10 | 1.0 | 0.12 | 0.10 | ○ | 3 |
| Example 2 | 38:2:60 | 150 | 5 | 1.0 | 0.14 | 0.11 | ○-△ | 2 |
| Example 3 | 38:2:60 | 20 | 10 | 0.5 | 0.12 | 0.07 | ○ | 3 |
| Example 4 | 38:2:60 | 150 | 2 | 1.0 | 0.19 | 0.15 | △ | 2 |
| Com. Ex. 1 | 38:2:60 | 150 | 0 | 1.0 | 0.20 | 0.15 | △ | 1 |
| Com. Ex. 2 | 38:2:60 | 13 | 10 | 0.2 | 0.20 | 0.09 | ○ | 1 |

[1]The outer surface area was measured by the BET method.
[2]As the numeral value increases, the reaction activity of the catalyst increases.
[3]As the numeral value decreases, the reaction selectivity of the catalyst increases.
[4]Moldability was determined by the fluidity of the catalyst precursor powder during the production of pellets and the presence or absence of a stick at the side surface of the pellets obtained.
○: Very good; the fluidity of the raw material powder is good, and no stick forms.
○-△: Good; the fluidity of the raw material powder is slightly bad, and no stick forms.
△: Slightly bad; the fluidity of the raw material powder is bad, and sticks form at the side surface of the pellet.
[5]Squeezing strength after recover of reaction was measured with Kiya-type hardness tester (mfd. by Kiya Seisakusho) to obtain the average value out of ten tests. As the value increases, the strength increases.

EXAMPLE 5

300 g of isopropyl alcohol and 135 g of titanium oxide (prepared by hydrolyzing titanium sulfate; burning temperature: 350° C.; surface area by the BET method: 150 m$^2$/g) were placed in a 10 liter separatory flask to form a suspension. 48.0 g (13.5 g calculated as titanium oxide) of tetraisopropyl titanate [((CH$_3$)$_2$CHO)$_4$Ti] was added to the suspension at 10% by weight to the titanium oxide calculated as titanium oxide, followed by sufficient stirring. Thereafter, 3 liter of ion-exchanged water was added dropwise to the suspension at room temperature, and the tetraisopropyl titanate in the system was completely hydrolyzed.

After distilling off isopropyl alcohol in the system, the temperature of the residue was raised to 98° C. with stirring. Then, a solution formed by dissolving 252.2 g (93 g as CuO) of copper nitrate trihydrate, 24.7 g (6.75 g as ZnO) of zinc nitrate hexahydrate, and 13.8 g (8.1 g as BaO) of barium nitrate in one liter of ion-exchanged water and an aqueous 10% sodium carbonate solution were simultaneously added to the foregoing carrier suspension heated to 98° C. to provide a catalyst precursor slurry having pH of 9. Precipitates were recovered from the slurry by filtration, sufficiently washed with water, and dried to provide a powder. The powder obtained was formed into pellets having a diameter of 3 mm, and the pellets were burned for 2 hours at a temperature of 450° C. in an oxidizing atmosphere. The catalyst precursor obtained had the following weight composition:

CuO:ZnO:BaO:TiO$_2$=33.7%:2.7%:3 3%:60.3%
(CuO:ZnO:BaO=1:0.08:0.10)

Evaluation of Catalyst Activity and Selectivity 15 g of the foregoing pelleted catalyst precursor together with 200 g of lauryl alcohol were placed in an autoclave-type basket reactor, and the reduction activation of the catalyst precursor was carried out at a hydrogen pressure of 10 kg/cm$^2$ (gauge pressure) and a temperature of 200° C. for 2 hours under a hydrogen stream.

After finishing the reduction, lauryl alcohol was replaced with 200 g of palm kernel methyl ether [saponification value (SV)=242 mg KOH/g], the reaction was carried out under a hydrogen stream at a hydrogen pressure of 230 kg/cm$^2$ (gauge pressure), a reaction temperature of 250° C., and a stirring rate of 900 r.p.m., and the primary reaction rate constant k [Hr$^{-1}$] was calculated from SV with the passage of time and was used as an indicator of the catalyst activity.

Also, the sample was analyzed with capillary gas chromatography with the passage of time, and the content (%) of methyl ether and hydrocarbon when the saponification value (SV) was 10 mg KOH/g was obtained using the analysis value and was used as an indication of the catalyst selectivity. The results obtained are shown in Table 2.

EXAMPLES 6 and 7 and COMPARISON EXAMPLE 3

By following the same procedure as in Example 5 except that the amount of barium sulfate was changed as shown in Table 2, catalyst precursors were obtained, and the activity and the selectivity of each catalyst were evaluated as in Example 5. The results obtained are shown in Table 2.

EXAMPLES 8 to 13

By following the same procedure as in Example 5 except that the nitrate of each of Mg and Ca as the elements of group IIa, Y as the element of group IIIb, La and Ce as the lanthanide elements, and Th as the actinide element was used in place of Ba as the element of group IIa of the periodic table such that 3.3% calculated as each oxide was incorporated in each catalyst precursor, each catalyst precursor containing each element in place of Ba was obtained. Using each of the catalyst precursors, the activity and the selectivity of the catalyst were evaluated as in Example 5. The results are shown in Table 2.

COMPARISON EXAMPLE 4

300 g of isopropyl alcohol and 22.2 g of titanium oxide (burning temperature: 350° C.; surface area by the BET method: 150 m$^2$/g) were placed in a 10 liter separatory flask to form a suspension. 7.8 g (2.2 g calculated as titanium oxide) of tetraisopropyl titanate [((CH$_3$)$_2$CHO)$_4$Ti] was added to the suspension at 10% by weight calculated as titanium oxide based on the weight of the foregoing titanium oxide base material, followed by sufficient stirring. 3 liter of ion-exchanged water was added thereto at room temperature, and the tetraisopropyl titanate in the system was completely hydrolyzed.

After distilling off isopropyl alcohol in the system, the temperature of the residue was raised to 98° C. with stirring. Then, a solution formed by dissolving 252.2 g (83 g as CuO) of copper nitrate trihydrate, 24.7 g (6.75 g as ZnO) of zinc nitrate hexahydrate, and 13.8 g (8.1 g as BaO) of barium nitrate in one liter of ion-exchanged water and an aqueous 10% sodium carbonate solution were simultaneously added dropwise to the foregoing carrier suspension heated to 98° C. to provide a catalyst precursor slurry having pH of 9. Precipitates were recovered from the slurry by filtration, sufficiently washed with water, and dried. The powder thus obtained was formed into pellets having a diameter of 3 mm, and the pellets were burned at 450° C. for 2 hours under an oxidizing atmosphere. The catalyst precursor obtained had the following weight composition:

CuO:ZnO:BaO:TiO$_2$=67.9%:5.5%:6.6%:20.0%
(Cuo:ZnO:BaO=1:0.08:0.10)

Using the foregoing catalyst precursor, the activity and the selectivity of the catalyst were evaluated as in Example 5. The results are shown in Table 2.

COMPARISON EXAMPLE 5

By following the same procedure as in Example 5 except that titanium oxide having a surface area of 13 m$^2$/g as determined by the BET method was used in place of titanium oxide having a surface area of 150 m$^2$/g by the BET method, a catalyst precursor was obtained. The activity and the selectivity of the catalyst were evaluated as in Example 5. The results obtained are shown in Table 2.

TABLE 2

| Catalyst Precursor Composition (weight ratio) | Base Material Outer Surface Area (m$^2$/g) | Coated Amount to Base Material (%) | Rate Constant K*1 (Hr$^{-1}$) | Reaction Selectivity*2 Methyl Ether (%) | Hydrocarbon (%) |
|---|---|---|---|---|---|
| Ex. 5 CuO:ZnO:BaO:TiO$_2$ = | 150 | 10 | 1.0 | 0.055 | 0.12 |

TABLE 2-continued

| | Catalyst Precursor Composition (weight ratio) | Base Material Outer Surface Area ($m^2/g$) | Coated Amount to Base Material (%) | Rate Constant $K^{*1}$ ($Hr^{-1}$) | Reaction Selectivity$^{*2}$ Methyl Ether (%) | Hydrocarbon (%) |
|---|---|---|---|---|---|---|
| | 33.7%:2.7%:3.3%:60.3% (CuO:ZnO:BaO = 1:0.08:0.10) | | | | | |
| Ex. 6 | CuO:ZnO:BaO:TiO$_2$ = 33.0%:2.7%:5.4%:58.9% (CuO:ZnO:BaO = 1:0.08:0.16) | 150 | 10 | 0.9 | 0.055 | 0.12 |
| Ex. 7 | CuO:ZnO:BaO:TiO$_2$ = 34.5%:2.8%:1.6%:61.1% (CuO:ZnO:BaO = 1:0.08:0.05) | 150 | 10 | 1.0 | 0.062 | 0.12 |
| Com. Ex. 3 | CuO:ZnO:BaO:TiO$_2$ = 31.5%:2.6%:9.5%:56.4% (CuO:ZnO:BaO = 1:0.08:0.30) | 150 | 10 | 0.4 | 0.055 | 0.12 |
| Ex. 8 | CuO:ZnO:MgO:TiO$_2$ = 33.7%:2.7%:3.3%:60.3% (CuO:ZnO:MgO = 1:0.08:0.10) | 150 | 10 | 0.9 | 0.055 | 0.12 |
| Ex. 9 | CuO:ZnO:CaO:TiO$_2$ = 33.7%:2.7%:3.3%:60.3% (CuO:ZnO:CaO = 1:0.08:0.10) | 150 | 10 | 0.9 | 0.055 | 0.13 |
| Ex. 10 | CuO:ZnO:Y$_2$O$_3$:TiO$_2$ = 33.7%:2.7%:3.3%:60.3% (CuO:ZnO:Y$_2$O$_3$ = 1:0.08:0.10) | 150 | 10 | 1.1 | 0.052 | 0.12 |
| Ex. 11 | CuO:ZnO:La$_2$O$_3$:TiO$_2$ = 33.7%:2.7%:3.3%:60.3% (CuO:ZnO:La$_2$O$_3$ = 1:0.08:0.10) | 150 | 10 | 1.0 | 0.060 | 0.12 |
| Ex. 12 | CuO:ZnO:CeO$_2$:TiO$_2$ = 33.7%:2.7%:3.3%:60.3% (CuO:ZnO:CeO$_2$ = 1:0.08:0.10) | 150 | 10 | 1.0 | 0.058 | 0.12 |
| Ex. 13 | CuO:ZnO:ThO$_2$:TiO$_2$ = 33.7%:2.7%:3.3%:60.3% (CuO:ZnO:ThO$_2$ = 1:0.08:0.10) | 150 | 10 | 0.9 | 0.062 | 0.12 |
| Com. Ex. 4 | CuO:ZnO:BaO:TiO$_2$ = 67.9%:5.5%:6.6%:20.0% (CuO:ZnO:BaO = 1:0.08:0.10) | 150 | 10 | 0.3 | 0.060 | 0.12 |
| Com. Ex. 5 | CuO:ZnO:BaO:TiO$_2$ = 33.7%:2.7%:3.3%:60.3% (CuO:ZnO:BaO = 1:0.08:0.10) | 13 | 10 | 0.3 | 0.055 | 0.12 |

$^{*1}$As the numeral value increases, the reaction activity of the catalyst increases.
$^{*2}$As the numeral value decreases, the reaction selectivity of the catalyst increases.

Based on the results shown in Table 2, it can be seen that comparison products 3, 4 and 5 provide excellent catalytic selectivity but are unsuitable for practical use for purposes of activity.

While the invention has been described in detail and with reference to specific embodiments thereof, it will be apparent to one skilled in the art that various changes and modifications can be made therein without departing from the spirit and scope thereof.

What is claimed is:

1. A process for producing a hydrogenation reaction catalyst precursor, comprising the steps of:

(i) coating the outer surface of at least one of a first titanium oxide and a first titanium hydroxide having an outer surface area of at least 15 $m^2/g$ with at least one of a second titanium oxide and a second titanium hydroxide formed by hydrolyzing at least one of a titanium alkoxide represented by Formula (I) and a titanium alkoxo acid represented by Formula (II) to prepare a catalyst carrier (A);

$$Ti(OR)_4 \qquad (I)$$

wherein R represents an alkyl group having from 1 to 18 carbon atoms or an aryl group, $$H_2[Ti(OR)_6] \qquad (II)$$

wherein R has the same meaning as above;

(ii) applying a metal oxide composition (B) comprising copper oxide and optionally at least one of zinc oxide and at least one oxide of a metal selected from an element of group IIa of the periodic table, an element of group IIIb of the periodic table, a lanthanide element, and an actinide element in a weight ratio of 100:(0 to 25):(0 to 25), onto the catalyst carrier (A) obtained in step (i), or mixing the metal oxide composition (B) with the catalyst carrier (A) at a weight ratio of (B)/(A)=15/85 to 65/35 to obtain a hydrogenation reaction catalyst precursor.

2. A process for producing a hydrogenation reaction catalyst precursor as in claim 1, wherein the amount of the at least one of a second titanium oxide and a second titanium hydroxide is from 5 to 100% by weight, based on the weight of the at least one of a first titanium oxide and a first titanium hydroxide.

3. A process for producing a hydrogenation reaction catalyst precursor as in claim 2, wherein the amount of the at least one of a second titanium oxide and a second titanium hydroxide is from 10 to 50% by weight, based on the weight of the at least one of a first titanium oxide and a first titanium hydroxide.

4. A process for producing a hydrogenation reaction catalyst precursor as in claim 1, wherein the outer surface area of the at least one of a first titanium oxide and a first titanium hydroxide is at least 50 $m^2/g$.

5. A process for producing a hydrogenation reaction catalyst precursor as in claim 1, wherein the metal oxide composition (B) comprises copper oxide and optionally at least one of zinc oxide and at least one oxide of a metal selected from an element of group IIa of the periodic table, an element of group IIIb of the periodic table, a lanthanide element, and an actinide element in a weight ratio of 100:(1 to 20):(1 to 20).

6. A process for producing a hydrogenation reaction catalyst precursor as in claim 1, wherein the metal oxide composition (B) further comprises at least one of tungsten oxide and molybdenum oxide.

7. A process for producing a hydrogenation reaction catalyst precursor as in claim 1, wherein the catalyst precursor is in the form of a powder or pellets.

* * * * *